US007106867B2

(12) United States Patent
Daly

(10) Patent No.: US 7,106,867 B2
(45) Date of Patent: Sep. 12, 2006

(54) ACTIVE NOISE CANCELLATION FOR A VEHICLE INDUCTION SYSTEM HAVING SELECTABLE ENGINE NOISE PROFILE

(75) Inventor: Paul D. Daly, Troy, MI (US)

(73) Assignee: Siemens VDO Automotive Inc., Chatham (CA)

( * ) Notice: Subject to any disclaimer, the term of this patent is extended or adjusted under 35 U.S.C. 154(b) by 672 days.

(21) Appl. No.: 10/092,076

(22) Filed: Mar. 6, 2002

(65) Prior Publication Data

US 2002/0168071 A1 Nov. 14, 2002

Related U.S. Application Data

(60) Provisional application No. 60/289,298, filed on May 8, 2001.

(51) Int. Cl.
*A61F 11/06* (2006.01)

(52) U.S. Cl. .................................... 381/71.4; 381/71.5

(58) Field of Classification Search .............. 381/71.4, 381/71.1, 71.8, 71.5
See application file for complete search history.

(56) References Cited

U.S. PATENT DOCUMENTS

| | | | | |
|---|---|---|---|---|
| 5,617,315 | A * | 4/1997 | Nakao et al. | 381/71.4 |
| 5,841,876 | A * | 11/1998 | Gifford et al. | 381/71.14 |
| 6,259,792 | B1 * | 7/2001 | Lambrecht | 381/73.1 |
| 6,688,422 | B1 * | 2/2004 | Fuesser et al. | 381/71.4 |
| 2002/0197955 | A1 * | 12/2002 | Witkowski et al. | 455/41 |

FOREIGN PATENT DOCUMENTS

| | | | |
|---|---|---|---|
| DE | 3420463 | A1 | 12/1985 |
| EP | 0 749 108 | A1 | 12/1996 |
| GB | 2351634 | A | 1/2001 |
| WO | 01/29819 | A1 | 4/2001 |

OTHER PUBLICATIONS

European Search Report, Sep. 10, 2003.

* cited by examiner

*Primary Examiner*—Brian T. Pendleton

(57) ABSTRACT

An active noise cancellation system (26) for controlling engine noise propagation through a vehicle induction system (32) is customizable to achieve a desired engine noise profile. A controller (34) of the active noise cancellation system drives a speaker (36) to generate a noise cancellation sound in a manner consistent with an individual's indicated preference for a specific type of available engine noise profile. By customizing how the speaker is driven, the system customizes the resulting engine noise heard in the passenger compartment. In one example, the system is customizable using a hand held communication device (24) such as a cell phone, a personal digital assistant or a so-called palm top computer. In another example, a resident communication bus on the vehicle is accessed through a user communication interface (28) supported on the vehicle.

20 Claims, 2 Drawing Sheets

ACTIVE NOISE CANCELLATION FOR A VEHICLE INDUCTION SYSTEM HAVING SELECTABLE ENGINE NOISE PROFILE

CROSS REFERENCE TO RELATED APPLICATIONS

This application claims priority to U.S. Provisional Application No. 60/289,298, which was filed on May 8, 2001.

BACKGROUND OF THE INVENTION

This invention generally relates to active noise cancellation in a vehicle induction system. More particularly, this invention relates to active noise cancellation providing a selectable engine noise profile.

Moderm day vehicles typically include an air induction system. One drawback of air induction systems is that engine noise frequently travels through the air induction system and emanates out of the mouth of the air intake such that the noises are noticeable in the passenger compartment of the vehicle. Various efforts have been made to reduce the amount of engine noise traveling through the air induction system. Some arrangements include passive devices such as expansion chambers and Helmholtz resonators. Other efforts include active methods such as anti-noise generators.

Typical active systems include a speaker that generates a sound to attenuate engine noise. The sound from the speaker is typically out of phase with the engine noise and combines with the engine noise. The result is a reduced noise in the air induction system, which results in less noise transmission into the passenger compartment.

Most active noise cancellation systems are preset by a vehicle manufacturer or supplier to achieve a desired amount of noise reduction. The choice for setting the active noise cancellation system is typically made by one or more technicians utilizing a test vehicle having a lap top computer, for example, appropriately coupled with the controller of the test vehicle active noise cancellation system. The technician is able to interface with the active noise system controller to adjust the performance of the active noise system as needed. This process provides a standard for presetting similar systems. Such settings are typically preprogrammed into the controllers of active noise cancellations systems subsequently provided to customers.

The eventual customer or vehicle owner is unable to adjust the performance of the active noise cancellation system. This invention provides an enhanced feature recognizing that some individuals may desire to customize the performance of the active noise cancellation system to achieve a desired engine noise profile.

SUMMARY OF THE INVENTION

In general terms, this invention is an active noise cancellation system that provides an individual the ability to adjust the active noise cancellation system to select the engine noise profile heard by those in the passenger compartment of the vehicle.

One example system designed according to this invention includes a speaker that generates a sound for attenuating engine noise. A controller selectively drives the speaker to generate a noise control sound in the active noise cancellation system. The noise control sound controls the engine noise profile heard by the driver and any other passengers present in the passenger compartment of the vehicle. The controller has a communication portion that is responsive to a selection from an individual who indicates one of several available engine noise profiles as the preferred noise profile. The controller drives the speaker according to the individual's indicated preference.

In one example, the communication portion of the controller has a modem function such that it operates as a cell phone. An individual is therefore able to access the customizing feature of the active noise cancellation system by dialing the appropriate cell phone number and providing input to the controller in this manner. In another example, an individual is able to use a handheld personal digital assistant device to interface with the controller of the active noise cancellation system so that the engine noise profile (i.e., the type of engine sound heard in the passenger compartment) can be selected.

The various features and advantages of this invention will become apparent to those skilled in the art from the following detailed description of the currently preferred embodiments. The drawings that accompany the detailed description can be briefly described as follows.

DETAILED DESCRIPTION OF THE PREFERRED EMBODIMENTS

Figure 1:
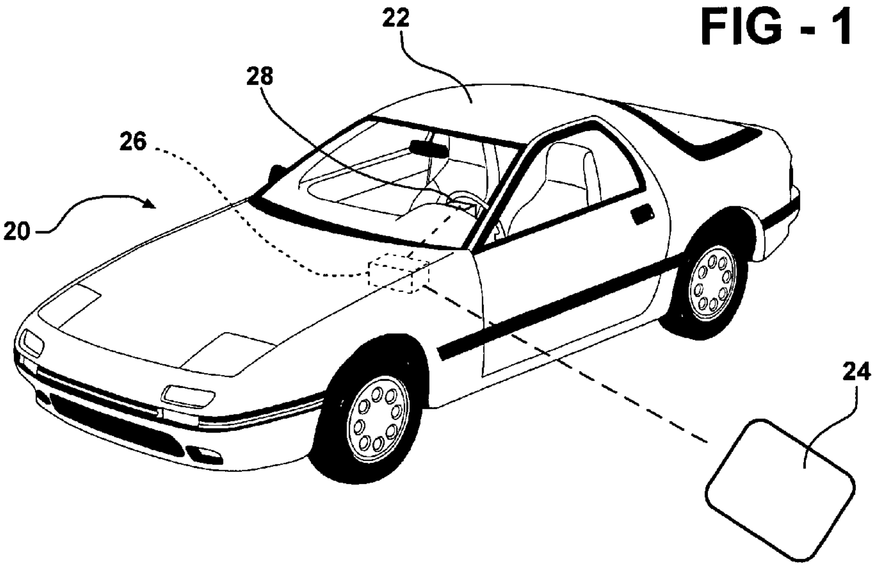
FIG. 1 diagrammatically illustrates a vehicle active noise cancellation system designed according to one example embodiment of this invention.

FIG. 1 schematically illustrates an active noise cancellation system 20 for use on a vehicle 22. A hand held device 24 facilitates communications with appropriate portions of the active noise cancellation system 26 supported on the vehicle 22. The handheld communication device 24 may be a cell phone, a personal digital assistant or a so-called palm top computer, for example. The handheld communication device 24 may communicate using wireless technologies such as bluetooth technology.

The illustrated vehicle 22 also includes a user interface 28 supported in the interior of the vehicle so that an individual may provide information to the appropriate portions of the active noise cancellation system 26 by using the user interface 28. The interface 28 preferably includes an input portion such as a keypad or a touch screen. In one example, the user interface 28 is a cell phone.

The active noise cancellation system 26 communicates with either type of device (i.e., a handheld communication device 24 that can be remotely located from the vehicle 22 or a communication device 28 supported within the vehicle 22) or both depending on the needs of a particular situation.

Figure 2:
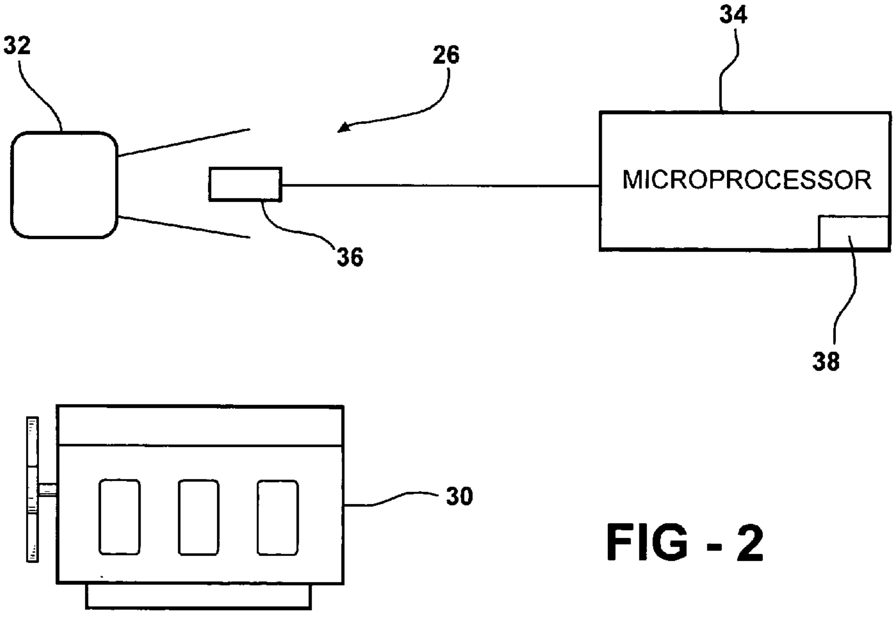
FIG. 2 schematically illustrates selected portions of the embodiment of FIG. 1.

As can be appreciated from FIG. 2, the active noise cancellation system 26 includes some conventional components for canceling out engine noises from the engine 30 that are otherwise promulgated through the air induction system 32 in a known manner. The active noise cancellation system 26 includes a controller 34 that is programmed to cause the active noise cancellation system to operate in a desired manner. The controller 34 drives a speaker 36 to generate a noise cancellation signal or noise attenuating sound that operates to attenuate the engine noise otherwise propagated through the air induction system.

In the illustrated example, the controller 34 includes a communication portion 38 that facilitates communications between the controller 34 and an individual using a handheld communication device 24 or a vehicle-mounted communication interface 28, for example. Example types of communication portions include a serial data interface or a modem (i.e., a so-called cell phone chip). Although the communication portion 38 is schematically illustrated as part of the controller 34, separate components, software or both may be used to realize the function of the communication portion 38. Those skilled in the art who have the benefit of this description will be able to select from among commercially available components or to custom design circuitry or software to meet the needs of their particular situation.

The controller 34 preferably is preprogrammed to accommodate a plurality of different engine noise profile selections. For example, one vehicle owner may prefer to experience an engine noise profile that resembles a racecar or sporty performance car. Another individual, on the other hand, may prefer a very quiet, luxury ride where minimal engine noise is experienced in the passenger compartment. The controller 34 preferably is programmed to accommodate either individual's preference, among others. Accordingly, the controller 34 adapts or customizes the performance of the active noise cancellation system 26 based upon the individual's preference.

In the illustrated example, an individual may use the handheld communication device 24 to communicate through the communication portion 38 of the active noise cancellation system 26. The individual provides a selection of one of several available noise profiles. The controller 34 determines the individual's preference and customizes the manner in which the speaker 36 is driven so that the noise attenuation results in an engine noise profile consistent with the individual's indicated preference.

Figure 3:
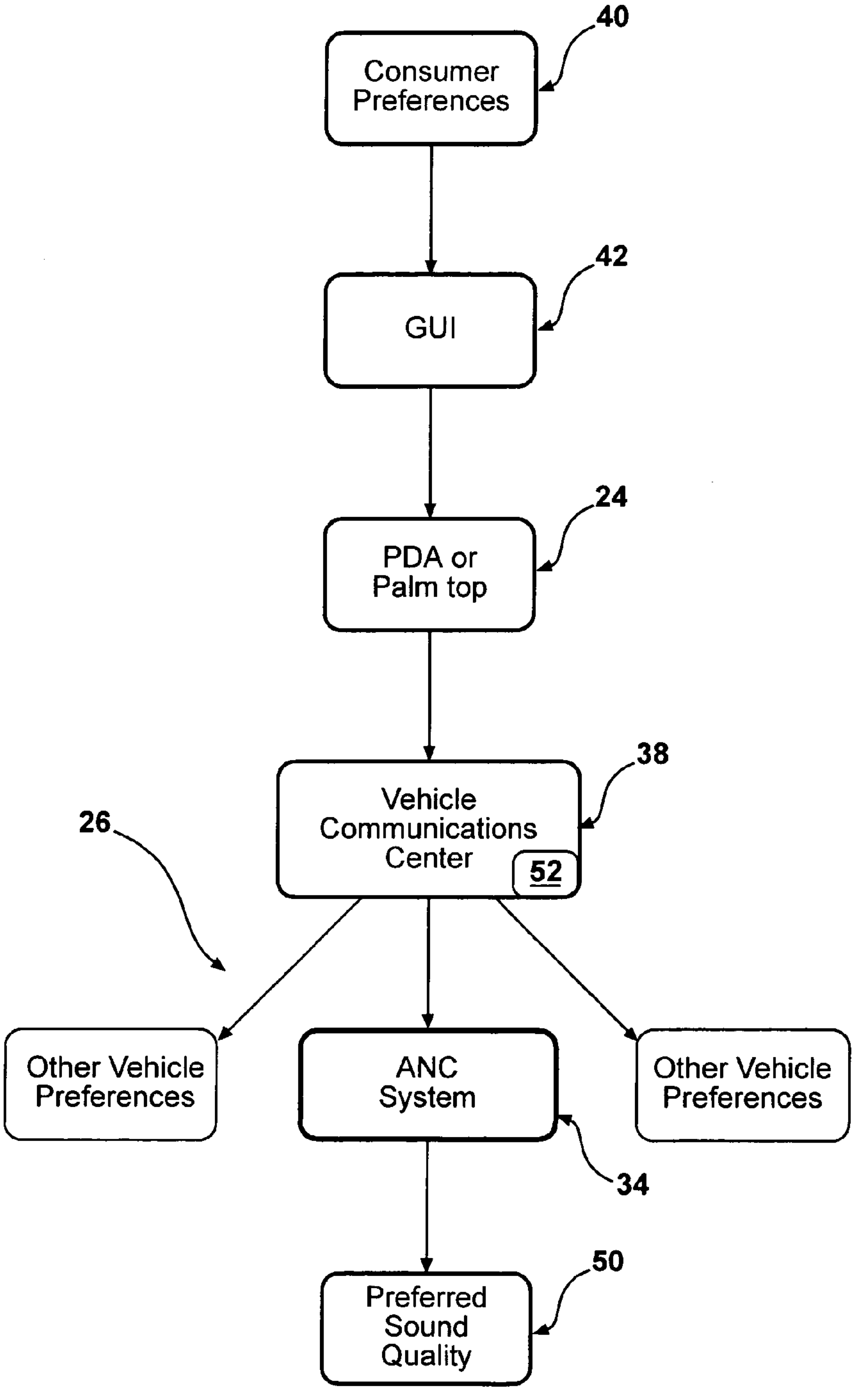
FIG. 3 schematically illustrates one example communication strategy of an active noise cancellation system designed according to this invention.

This can be appreciated from FIG. 3, which schematically shows one type of communication strategy in a system designed according to this invention. The available consumer preferences 40 preferably are presented to the individual through a graphical user interface 42 on the handheld communication device 24. The communication of the user's preference then is accomplished through the communication portion 38 and provided to the controller 34, which responsively drives the speaker 36 to provide the desired engine noise profile at 50.

As mentioned above, the communication portion 38 may be a resident part or dedicated portion of the controller 34 electronics. Alternatively, the communication portion 38 may be incorporated into the communication interface 28 supported on the vehicle. The communication interface 28 allows an individual to instruct the controller 34 how to customize the engine noise profile. In one example, a serial communication is provided through the interface 28 over a conventional CAN bus communication line.

In one example system, the user simply accesses the interface 28 within the vehicle to provide the information necessary to communicate the individual's preferred engine noise profile. In another example, a remote communication device 24 connects to the interface 28 using a conventional telephone communication such as through cellular telephone communications. In another example, the communication module 38 has its own phone number that can be accessed using the "in-vehicle" interface 28 or a remote communication device 24. Those skilled in the art who have the benefit of this description will be able to select from the various possibilities to achieve the desired communication protocol.

In one example, the communication portion 38 is part of a network that allows communication with various portions of the vehicle for an individual to customize the performance of the corresponding electronics, for example. In such an example, the communication network includes a tracking portion 52 that provides information regarding an individual's access to the active noise cancellation system electronics. The tracking module provides information, for example, on the number of changes made by the individual to the engine noise profile. Such information is useful, for example, in assessing a charge to an individual for each time that the engine noise profile is changed. Another use of such information is to determine demographic information regarding customer preferences to then make adjustments to subsequently offered products to meet customer demands.

The inventive arrangement provides an active noise cancellation system that is selectively customizable by an individual to achieve a desired engine noise profile, which will best suit the individual's preferences to maximize a satisfying experience while driving the vehicle.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

I claim:

1. An active noise cancellation system for use in a vehicle air induction system, comprising:

a vehicle air induction system component;

a speaker that selectively generates a noise control sound that influences a noise associated with the vehicle air induction system component and controls an engine sound heard inside the vehicle;

a controller that selectively drives the speaker to generate the noise control sound; and a communication portion that is adapted to communicate a selection from an individual indicating a selected sound as one of several available audible engine sounds to the controller which responsively drives the speaker to achieve the selected sound.

2. The system of claim 1, including a user communication interface supported on the vehicle that communicates with the communication portion and wherein the user communication interface includes an input portion that allows an individual to indicate a desired one of the available engine sounds.

3. The system of claim 1, including a user communication interface that comprises a modem and wherein the controller communicates with the modem.

4. The system of claim 1, including a user communication interface that comprises an electronic personal digital assistant device and wherein the communication portion controller communicates with the electronic personal digital assistant device.

5. The system of claim 1, wherein the communication portion communicates wirelessly with a communication device that is independent of the active noise cancellation system.

6. The system of claim 5, wherein the communication portion has an identifier that is accessible by a user through the independent communication device.

7. The system of claim 6, wherein the identifier comprises a phone number that is accessible by another telecommunication device for communication with the active noise cancellation system.

8. A method of controlling a perceived engine noise profile, comprising the steps of:

providing an active noise cancellation system in a vehicle air induction system;

determining a user preference for at least one of a plurality of available audible engine noise profiles; and automatically adjusting a noise control sound provided by the noise cancellation system responsive to the user preference so that a resulting audible engine noise profile heard by the user corresponds to the user preference.

9. The method of claim 8, including programing a controller to selectively drive a speaker of the noise cancellation system in one of a plurality of predetermined manners, each of the manners corresponding to one of the available noise profiles.

10. The method of claim 9, including programming the controller to drive the speaker to produce a sound that causes the resulting engine noise profile to be one of a sport engine noise profile or a quiet performance engine noise profile.

11. The method of claim 8, including communicating with a user interface supported on the vehicle to determine the user preference.

12. The method of claim 8, including communicating with a remotely located communication device that is independent of the noise cancellation system to determine the user preference.

13. The method of claim 12, including using wireless communication.

14. An active noise cancellation system for controlling a perceived engine noise profile that is heard by a driver of a vehicle, comprising:

at least one vehicle air induction system component;

a speaker associated with the at least one air induction system component, the speaker generates at least one of a plurality of available noise control sounds that correspond to a plurality of available audible engine noise profiles;

a controller that selectively drives the speaker such that the perceived engine noise profile corresponds to a user selection of one of the available audible engine noise profiles; and a communication network that facilitates communication between an individual and the controller.

15. The system of claim 14, wherein the communication network includes a cell phone chip associated with the controller, the cell phone chip providing a unique communication identifier to the controller such that an individual can communicate with the controller through the network.

16. The system of claim 15, including a tracking module that tracks use of the communication network and provides information regarding access to the network to selectively adjust the noise profile.

17. The system of claim 14, wherein the communication network includes a user communication interface supported on the vehicle that communicates with the controller and wherein the user communication interface includes an input portion that allows an individual to indicate a desired one of the available noise profiles.

18. The system of claim 14, including a user communication interface that comprises a cell phone and wherein the communication network receives user input from the cell phone.

19. The system of claim 14, including a user communication interface that comprises an electronic personal digital assistant device and wherein the communication network receives user input from the electronic personal digital assistant device.

20. The system of claim 14, including a unique identifier and wherein the communication network uses the identifier to facilitate communication between a user and the controller through a remote communication device that is independent of the noise cancellation system.

* * * * *